US005660983A

United States Patent [19]

Levings, III et al.

[11] Patent Number: 5,660,983

[45] Date of Patent: Aug. 26, 1997

[54] MAIZE CYTOPLASMIC MALE STERILITY TYPE T (CMS-T) MITOCHONDRIA DNA

[75] Inventors: Charles S. Levings, III; Ralph Dewey, both of Raleigh, N.C.

[73] Assignees: Mycogen Plant Science, Inc., San Diego, Calif.; North Carolina State University, Raleigh, N.C.

[21] Appl. No.: 345,264

[22] Filed: Nov. 23, 1994

Related U.S. Application Data

[63] Continuation of Ser. No. 716,645, Jun. 17, 1991, abandoned, which is a continuation-in-part of Ser. No. 937,926, Dec. 4, 1986, abandoned.

[51] Int. Cl.$^{6}$ .......................... C07H 21/04; C12N 15/70; C12Q 1/68

[52] U.S. Cl. .......................... 435/6; 435/320.1; 536/23.1; 536/23.6; 536/24.3

[58] Field of Search .................................. 536/23.1, 23.6, 536/24.3; 435/6, 320.1

[56] References Cited

U.S. PATENT DOCUMENTS

| | | | |
|---|---|---|---|
| 4,358,535 | 11/1982 | Falkow et al. | 435/6 |
| 4,581,333 | 4/1986 | Kourilsky et al. | 435/6 |

FOREIGN PATENT DOCUMENTS

| | | | |
|---|---|---|---|
| 0267279 | of 1988 | Japan | 435/320.1 |

OTHER PUBLICATIONS

Kemble et al. (1983) Nature 304:744.
Stern and Palmer (1984) Proc. Natl. Acad. Sci. USA 81:1946.
Gengenbach et al. (1977) Proc. Natl. Acad. Sci. USA 74:5113.
Brettell et al. (1979) Maydica 24:203–213.
Forde and Leaver (1980) Proc. Natl. Acad. Sci. USA 77:418–422.
Unbeck and Gengenbach (1983) Crop Sci 23:584.
Pring and Levings (1978) Genetics 89:121.
Dewey et al. (1985) Plant Physiol. 79:914.
Dale et al. (1984) Plasmid 11:141.
Kato et al. (1985) Curr Genet. 9:405.
Forde et al. (1978) Proc. Natl. Acad. Sci. USA 75(8):3841–3845.
Dewey et al. (1986) Cell 44:439–449.
Levings, C.S. III (1983) in Genetic Engineering of Plants (T. Kosuge, C.P. Meredith and A. Hollaender, eds. Plenum Press, New York, pp. 81–92.
Lonsdale et al. (1984) Nucl. Acids Res. 12:9249.
Stern and Lonsdale (1982) Nature 299:698.

*Primary Examiner*—Stephanie W. Zitomer
*Assistant Examiner*—Paul B. Tran
*Attorney, Agent, or Firm*—Saliwanchik, Lloyd & Saliwanchik

[57] ABSTRACT

Reagents and test methods for rapidly and specifically testing maize plants for the presence of T-type cms are provided. The reagent includes a novel nucleic acid segment whose sequence is uniquely arranged in mitochondrial DNA of cms-T maize. The segment, designated TURF 2H3, was cloned and vectors comprising TURF 2H3 provided. Subclones having sequences specific to cms-T mitochondrial DNA and the DNA and deduced amino acid sequences of ORI3, which is unique to T-type cytoplasm, are also provided.

15 Claims, 2 Drawing Sheets

MAIZE CYTOPLASMIC MALE STERILITY TYPE T (CMS-T) MITOCHONDRIA DNA

This application is a continuation of application of U.S. patent application Ser. No. 07/716,645, filed Jun. 17, 1991, now abandoned, which is a continuation-in-part application of U.S. patent application Ser. No. 06/937,926, filed Dec. 4, 1986, and now abandoned which application is incorporated by reference herein.

The invention relates to plant breeding and plant molecular biology; more specifically, to genetic constructions comprising a DNA sequence unique to, and/or diagnostic for, cytoplasmically-inherited male sterility, type T (cms-T), of maize (*Zea mays* L.). Male sterility is very useful to plant breeders for the production of hybrids, either for breeding or for hybrid seed production. Plants which do not produce fertile pollen can serve as the female parent in a cross, without the need for detasseling, hand-emasculation or chemical gametocide treatment, all of which are either labor-intensive, costly or both. However, for a sterility trait to be useful, it must be possible to maintain viable strains carrying the trait, and yet the trait must be expressible when needed.

Cytoplasmic male sterility (cms) is a well known phenomenon which fulfills the basic requirements (for review, see Levings, C. S. III (1983) in *Genetic Engineering of Plants* (T. Kosuge, C. P. Meredith and A. Hollaender, eds.) Plenum Press, New York, pp. 81–92). Cms has been most thoroughly studied and exploited in maize. Three distinct types of cms have been identified in maize, designated C, S and T. Of these, the latter has been found to provide a sufficient degree of sterility and stability of sterility to be of significant commercial utility. Some commercial use is also made of cms-C. The utility of cms-T is limited by the fact that maize strains and hybrids bearing the cms-T trait are specifically susceptible to the fungal pathogen *Bipolaris maydis* (*Helminthosporium maydis*) race T. *B. maydis* elaborates a pathotoxin that is toxic to maize carrying the cms-T trait (sometimes referred to as having T-cytoplasm). The use of cms-T for breeding, seed production or the incorporation into hybrids is limited to the western northern tier of states where corn blight caused by *B. maydis* does not occur.

The genes for cms traits are believed to be located in the mitochondrial genome (see Levings (1983) supra). Evidence from the prior art is insufficient to permit a conclusion as to whether any of the C, S or T traits is conferred by one, or more than one, gene. However, each of the three cms types can be restored to fertility by unique restorer genes (termed RF, for "restorer of fertility"), located in the nucleus. Each known restorer gene is specific to the type (C, S or T) of cms it restores. Two restorer genes are required to restore fertility to cms-T, termed Rf1 and Rf2. Both must be present for restoration and neither, acting alone, confers partial fertility. The biochemical mechanisms which bring about sterility or fertility are unknown. In genetic terms, the cms trait is non-Mendelian, and transmitted by the female parent. Restorers are inherited in Mendelian fashion and behave as dominant traits. The evidence to be found in the prior art is not sufficient to determine whether any structural relationship exists between cms genes and their restorers.

The commercial value of using cms is that it permits specific hybrids to be formed in field-grown plants. One parent (male-fertile) is the pollen source, while the other (male-sterile) is the female parent. Only two types of crosses can occur: the male-fertile parent either pollinating itself or the female parent. All plants used as female parent, therefore, give rise to hybrid progeny. In the absence of cms, some other means must be used to prevent self-pollination of the female parent. Hand and/or mechanical detasseling are used extensively in maize, but the labor cost is a significant and increasing part of seed production cost. For most crops hand-emasculation is too difficult and costly to be used on a commercial scale. Chemical gametocides have been developed (see, e.g., published European Patent Applications 031 176 and 049 971); however, their use is costly. Therefore, wherever it is possible to do so, use of cms is preferred for mating and testing hybrid plants and for producing commercial quantities of hybrid seeds.

The economic value of cms is sufficiently great that commercial breeding programs to identify and evaluate new sources and types of cms are being carried out for many crops including maize. In order for a plant breeder to distinguish cms genotypes, it is necessary to classify each new cms accession where, as in maize, more than one type of cms exists. Typically the classification is carried out by a series of crosses between a female cms parent and various male RF parents. Since restoration is cms type-specific, fertility in the offspring will only be observed in crosses with the corresponding RF parent. For example, a cms maize plant would be separately crossed with a set of male parents, each carrying a different RF gene, for restoring either T, S or C types of cms. The progeny plants must then be grown to sexual maturity to determine whether they are sterile or fertile. The process requires nearly two full generations to complete. Therefore, it would be advantageous to have a diagnostic test capable of identifying a specific cms genotype without the expense and delay of the standard plant crossing method currently in use.

Mitochondrial genomes of higher plants are larger and more complex than those of other eukaryotic organisms (Levings, C. S. III (1983) Cell 32:659). The complexity is due in part to intramolecular recombinational events in which populations of subgenomic circles are generated from a master genomic circle (Palmer and Shields, (1984) Nature 307:437; Lonsdale et al. (1984), Nucleic Acids Res. 12:9249). Large repeated sequences often appear to be the sites of intramolecular recombination (Lonsdale et al., 1984). Intergenomic rearrangements have also been reported involving the exchange of DNA between the chloroplast, nuclear and mitochondrial genomes of higher plants (Stern and Lonsdale, (1982) Nature 299:698; Kemble et al. (1983) Nature 304:744; Stern and Palmer, (1984) Proc. Natl. Acad. Sci. USA 81:1946).

The mitochondrial genome of *Zea mays* from normal (male fertile) cytoplasm is estimated to be 570 kilobases (kb) in length by cosmid mapping (Lonsdale et al., 1984). Restriction endonuclease digestion analysis of the mitochondrial DNA (mtDNA) from normal and mutant cytoplasms of maize, however, has revealed considerable heterogeneity among the different cytoplasms (Pring and Levings (1978) Genetics 89:121). MtDNA restriction fragment analysis of various members of the genus Zea shows recombinational events to be the major force accounting for the molecular heterogeneity among the species (Sederoff et al. (1981) Proc. Natl. Acad. Sci. USA 78:5953).

Maize carrying cms-T is unique in that in nature, an inseparable association between disease susceptibility to the fungal pathogen *Bipolaris maydis* (*Helminthosporium maydis*), race T, and male sterility appears to exist in this cytoplasm (Hooker et al. (1970) Plant Dis. Rep. 54:708; Gengenbach et al. (1977) Proc. Natl. Acad. Sci. USA 74:5113; Brettell et al. (1979) Maydica 24:203–213.)

In vitro protein synthesis studies with isolated mitochondria have revealed differences in the proteins produced by normal and T cytoplasms (Forde and Leaver (1980) Proc. Natl. Acad. Sci. USA 77:418–422). One-dimensional SDS gel electrophoresis has shown a 13,000 Mr protein product unique to T cytoplasm. In addition, a 21,000 Mr polypeptide observed in normal mitochondria is absent in T. The functions of these translational products have not been determined, although an involvement with cms has been suggested. The 13,000 Mr protein is apparently subject to nuclear regulation, since fertility restoration of the T cytoplasm with nuclear restorer genes Rf1 and Rf2 significantly suppresses synthesis of the 13,000 Mr product (Forde and Leaver, 1980 supra).

Regeneration studies with tissue cultures of cms-T maize have discovered interesting changes in disease resistance and the cms phenotype. Reversion from male sterility to male fertility often occurs in plants regenerated from callus culture (Gengenbach et al., 1977 supra); Brettell et al., 1979 supra). Moreover, reversion is invariably associated with a newly acquired resistance to the *B. maydis*, race T, pathogen. Frequently associated with reversion to the fertile, resistant phenotype is the loss of a 6.6 kb XhoI mtDNA fragment in digests of revertant plants (Umbeck and Gengenbach (1983) Crop Sci. 23:584).

No function has yet been ascribed to either the 13,000 Mr protein or the approximately 21,000 Mr protein. Whether either or both of these proteins actually contribute to the cms phenotype is unknown. Further, it is not known whether the 21,000 Mr protein contributes to the phenotype of susceptibility to *B. maydis* race T or to the resistance of non-T cytoplasmic genotypes to the pathogen. At present, no biochemical mechanism is known to explain the existence of cms, but it is now known that biochemical mechanism of susceptibility to *B. maydis* race T lies in the ORF13 gene product. It has been shown that the protein product of ORF13 is a membrane protein and that it confers sensitivity to the *B. maydis* toxin. When the ORF13 protein is expressed in an *Escherichia coli* host, the recombinant bacterial cells become sensitive. Recombinant *E. coli* cells treated with the *B. maydis* toxin exhibit Rubidium ion leakage, as do toxin-treated cms-T maize mitochondria. Mutant ORF13 sequences which do not confer toxin-sensitivity in corn mitochondria similarly do not render recombinant *E. coli* sensitive to the *B. maydis* toxin Braun et al. (1989) in *The Molecular Basis of Plant Development*, Alan R. Liss, Inc., pp. 79–85.

The 6.6 kb XhoI fragment described by Umbeck and Gengenbach (1983) has not been further characterized, either as to sequence or restriction map. There is no prior evidence as to whether any portion of the Umbeck and Gegenbach 6.6 kb XhoI fragment is transcribed or translated. Also, there is no prior evidence indicating whether any part or all of the nucleotide sequence of the fragment is unique to cms-T mitochondrial DNA, except for the creation or deletion of an XhoI site. Restriction endonuclease digestion analysis of mtDNA from normal and sterile cytoplasms of maize has revealed additional heterogeneity among the different cytoplasms (Pring and Levings (1978) Genetics 89:121). The maize mitochondrial genome of normal cytoplasm contains six major sequence reiterations, approximately 1 kb, 2 kb, 3 kb, 10 kb, 12 kb and 14 kb in length (Lonsdale, et al. (1984)). Each repeat is found twice within the master genomic circle. All except the 10 kb repeat are implicated in the formation of the smaller subgenomic circles. In the face of the substantial degree of genomic rearrangement occurring within the normal mtDNA, the mere existence of an unusual DNA restriction fragment is cms-T mtDNA cannot be interpreted without additional evidence relating the fragment to a function unique to cms-T.

SUMMARY OF THE INVENTION

The present invention provides a reagent and test methods for rapidly and specifically testing maize plants for the presence of T-type cms. The reagent includes a newly discovered nucleic acid segment (preferably DNA), the nucleotide sequence of which is uniquely arranged within the mitochondrial DNA of cms-T maize. By cloning that region of cms-T mitochondrial DNA whose sequence is uniquely arranged in cms-T, specific DNA segments of the unique region have been obtained in essentially pure form. Specifically, three restriction fragments, spanning a contiguous sequence of 3547 nucleotides, have been cloned. The region spanned by these fragments is designated TURF 2H3. Various subclones of TURF 2H3 have been inserted in plasmid vectors, thereby providing for replicating desired quantities of any desired segment of TURF 2H3 in a suitable host organism and further providing for specifically excising and purifying the segment. (A subclone of TURF 2H3 is defined herein as a cloned or synthesized DNA fragment having a nucleotide sequence of at least 10 contiguous nucleotides in length, corresponding to the sequence of a segment of TURF 2H3.) When labeled with an appropriate marker, the purified segment or a subclone thereof is used as a reagent in a hybridization reaction with restriction endonuclease-cleaved maize mitochondrial DNA to screen for cms-T-type cms in maize plants of unknown cytoplasmic genotype. Preferably a probe used in hybridization reactions is at least 14 nucleotides in length.

Accordingly the present invention provides a cloned DNA segment comprising the nucleotide sequence of TURF 2H3 or a subclone thereof, and also provides a DNA vector comprising inserted maize DNA consisting essentially of the nucleotide sequence of TURF 2H3 or a subclone thereof. The foregoing products of the invention are useful in a method for detecting T-type cytoplasm in a sample of maize seedling tissue, comprising the steps of: a) extracting mtDNA from the maize seedling tissue, b) digesting the mtDNA with a restriction endonuclease, thereby producing fragments of digested mtDNA having various molecular weights, c) fractionating the digested mtDNA according to molecular weight, d) hybridizing the mtDNA with probe DNA comprising labeled TURF 2H3 or a subclone thereof, e) measuring the approximate molecular weight of the fragment to which the probe DNA has hybridized, and f) comparing the approximate molecular weight measured in step e) with the molecular weight of a control fragment of cms-T mtDNA treated as in steps b)–e) whereby T-type cytoplasm is detected as the source of the mtDNA when the molecular weight measured in step e) corresponds to that of the control.

The invention also provides a DNA segment comprising ten contiguous nucleotides of the sequence of clone 913-T41. The DNA segment is useful in a method for detecting T-type cytoplasm in a sampling of maize seedling tissue comprising the steps of: (a) extracting sample mRNA from maize seedling tissue, (b) hybridizing the mRNA with probe DNA comprising a labeled DNA segment comprising at least 14 consecutive nucleotides of the sequence of clone 913-T41, (c) measuring whether the probe DNA specifically hybridizes to sample mRNA, after comparing the sample mRNA to control samples of normal and cms-T mRNA, whereby T-type cytoplasm is detected in the sample of maize seedling tissue when the amount of probe DNA hybridizing to the sample mRNA corresponds to the amount of probe DNA hybridizing to the control cms-T mRNA. Preferably for hybridization experiments, the probe is at least 14 bases long.

The cms-T-specific nucleotide sequences of the present invention can also be employed to generate primers for use in Polymerase Chain Reaction (PCR) Methods for the detection of cms-T mitochondria of maize by virtue of sequences unique to T-type cytoplasm or by virtue of sequences with lengths characteristic to T-type cytoplasm. Primer sequences are at least 18 bases in length, and preferably 20–24 bases in length; pairs of primers for use in PCR are taken from opposite DNA strands, from regions flanking the target region whose detection and/or amplification is desired.

BRIEF DESCRIPTION OF THE SEQUENCES

SEQ ID NO. 1 is a 17-mer corresponding to positions 1400–1416 of TURF 2H3 and is located in the middle of ORF 13.

SEQ ID NO. 2 is a 21-mer corresponding to positions 1235–1255 of TURF 2H3 and is located near the 5' end of ORF 13.

SEQ ID NO. 3 is a 17-mer which is the complementary nucleotide sequence to that of SEQ ID NO. 1.

SEQ ID NO. 4 is a 21-mer which is the nucleotide sequence complementary to that of SEQ ID NO. 2.

DETAILED DESCRIPTION OF THE INVENTION

Figure 1:
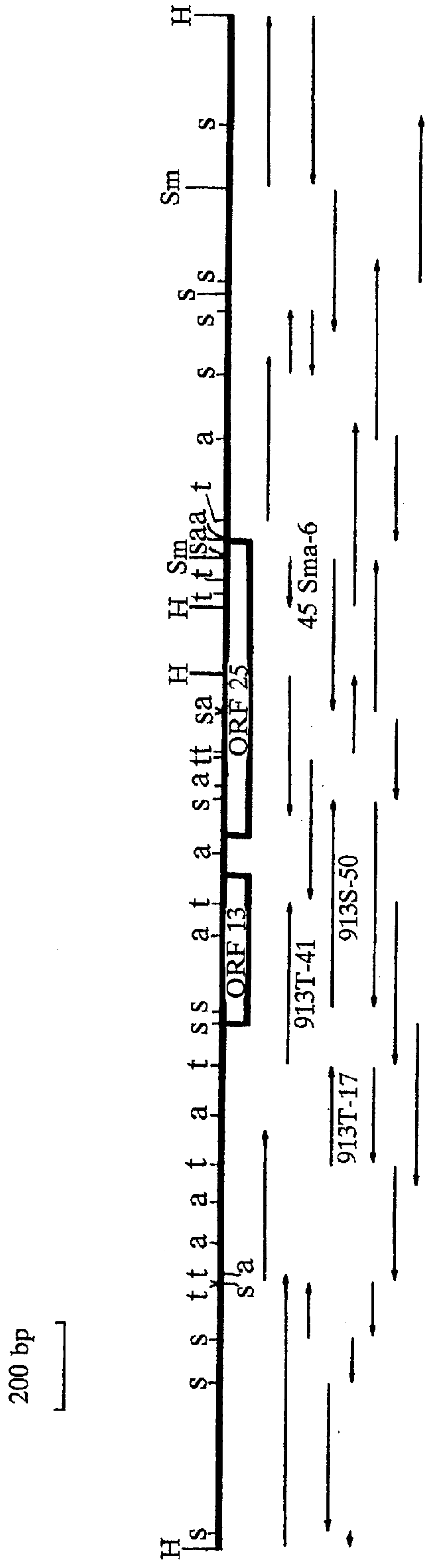
FIG. 1 illustrates the cms-T locus of the maize mitochondrial genome. Open reading frames are indicated by boxed regions. Arrows below the map show the direction and extent of sequence analysis from each restriction site. Clones referred to herein are designated with numbers. Restriction sites are indicated by vertical lines: a, AluI, H, HindIII; s, Sau3A: Sm, SmaI; t, TagI.

The present invention is based upon the cloning and sequence characterization of a DNA segment characteristic of cms-T maize mitochondrial DNA. The segment has several unusual characteristics. A region of it, essentially co-extensive with the subclone 913T-41 (see FIG. 1), is uniquely transcribed in cms-T maize mitochondria, as demonstrated by Northern hybridization studies revealing an mRNA found only in cms-T mitochondria and hybridizing only to DNA segments containing all or part of 913T-41. The characteristic segment has been named TURF 2H3, has a length of 3547 bp and has been completely sequenced. A map of TURF 2H3 showing certain structural features and subclones thereof is shown in FIG. 1 and the sequence of TURF 2H3 is shown in Table 1. In FIG. 1, open reading frames are indicated by boxed regions, arrows below the map show the direction and extent of sequence analysis from each restriction site. Clones cited elsewhere in the specification are designated with numbers. Restriction sites are designated by vertical lines: a is AluI, H is HindIII, s is Sau3A, Sm is SmaI and t is TaqI. In Table 1, sequences homologous with portions of atp6, a 26S ribosomal RNA gene and tobacco chloroplast tRNA-Arg are indicated by an asterisk. Sequence numbers of atp6 are in relation to the atp6 putative start codon (Dewey et al. (1985) Plant Physiol. 79:914). Sequence numbers of the 26S ribosomal RNA and tobacco tRNA-Arg genes are as published (Dale et al. (1984) Plasmid 11:141; Kato et al. (1985) Curr. Genet. 9:405). Points of recombination are designated with arrows. The predicted amino acid sequences of reading frames ORF13 and ORF25 are translated according to the mitochondrial genetic code of higher plants (Fox and Leaver (1981) Cell 26:315), beginning at the first ATG codon.

The entire sequence of TURF 2H3 is contained within a larger fragment of 9.0 kb generated by BamHI digestion of mitochondrial DNA, designated TURF 2B. Therefore, TURF 2H3 and subsequences thereof hybridize to a 9.0 kb band of BamHI-digested mitochondrial DNA in Southern (DNA:DNA) hybridizations.

Analysis of the TURF 2H3 sequence revealed the existence of two large open reading frames within a region of TURF 2H3 known to be transcribed. The first frame, designated ORF13, is located from positions 1161 to 1559, where a TGA stop codon occurs. According to recent studies, TGA is a termination codon in higher plant mitochondria (See Schuster and Brennicke (1985) Curr. Genet. 9:157; Braun and Levings (1985) Plant Physiol. 79:571). Assuming translation initiates with an AUG codon, ORF13 could start at position 1215 and encode a polypeptide 115 amino acids long with a predicted molecular weight of 12,961. A smaller polypeptide is predicted if initiation occurs at the next ATG, codon at position 1326. Because complex rearrangements of DNA have occurred in the formation of this region (see infra), the complete open reading frame is unique to cms-T. ORF13 is also in the segment of TURF 2H3 that is uniquely transcribed in T cytoplasm, (913T-41).

The second open reading frame, designated ORF25, extends from positions 1547 to 2302 where a TAG stop codon is encountered. ORF25 occurs in a different reading frame than ORF13 and overlaps with ORF13 from positions 1547 to 1559. The first ATG codon, however, is located at position 1640. Assuming translation begins with the ATG codon at position 1640, ORF25 could code for a protein 221 amino acids long with a predicted molecular weight of 24,675. The DNA sequence encoding ORF25 hybridizes to transcripts in all four cytoplasms (normal, cms-T, cms-S and cms-C). Sequences homologous to ORF25 DNA have been shown to exist in mtDNA from bean, wheat, pea and rice. Computer searches of the predicted translation products of ORF13 and ORF25 to amino acid sequences in the National Biomedical Research Foundation (NBRF) protein library detected no significant homologies.

Comparison of the TURF 2H3 nucleotide sequence with other known plant DNA sequences has revealed striking homologies to DNA of disparate sources including the 5' flank of the mitochondrial gene atp6, various portions of the flanking and coding regions of the mitochondrial 26S ribosomal RNA gene, and a chloroplast tRNA gene. Analysis of these homologies suggests that TURF 2H3 may have originated through a complex series of recombination events; a minimum of 7 recombination sites have been identified.

The first 1145 base pairs of TURF 2H3 are identical with the 5' flanking DNA sequence of atp6, extending from positions −1589 to −445, numbered with respect to the initiator ATG codon of the gene for ATPase subunit 6 (See Dewey, R. E. et al. (1985) Plant Physiol. 79:914). Further hybridization studies demonstrated that in normal, cms-S and cms-C genomes, only one copy of the atp6 gene is found, whereas in cms-T, at least that portion found within TURF 2H3 is repeated.

Three segments of TURF 2H3 were found to contain significant homology with sequences of the maize mitochondrial 26S ribosomal RNA gene or its flanking regions (See Dale, R. M. K et al. (1984) Plasmid 11:141). The first homologous segment occurs at the end of the long repeat common with atp6. Twenty-nine of thirty base pairs are identical between positions 1116 to 1145 of TURF 2H3 and a DNA segment in the 5' flanking region of the 26S ribosomal RNA gene (positions 450–479). The homology extends past the repeat when the comparison is made only between the 5' flanking sequences of atp6 and the 26S gene. An additional 11 base pair identity is observed between the atp6 and 26S gene 5' flanking regions interrupted only by a 5 bp duplication of the sequence TCTAC in atp6.

The second region of homology between TURF 2H3 and the 26S rRNA gene occurs between positions 1161 to 1477 of TURF 2H3 and a segment of the 3' flanking region of the 26S gene extending from positions 4170–4487. The sequence homology is 85%. Five mismatches in this region result from a 5 bp duplication of the sequence, TCTCA in the 26S 3' flanking sequence.

The third region of homology with the 26S rRNA gene is found between positions 1507–1564 of TURF 2H3 and positions 1055 and 1110 of the 26S gene. This homologous region, in contrast with the others, is located in the coding sequence of the 26S ribosomal RNA gene. Ninety-five percent homology is observed between these segments including a continuous stretch of 47 bp with perfect identity.

Significant homology has also been found between a fragment of TURF 2H3 and the chloroplast tRNA-Arg genes of tobacco, *Spirodela oligorhiza* and *Euglena gracilis* (See Kato, A. et al. (1985) Curr. Genet. 9:405; Keus, R. J. A. et al. (1984) Nucl. Acids Res. 12:5639; Orozco and Hallick (1982) J. Biol. Chem. 257:3265). The homology extends from positions 2260–2363 of TURF 2H3 and positions 713–812 of the tobacco gene. The region of TURF 2H3 is homologous with 37 bp of the tobacco tRNA-Arg 5' flank along with all of the coding region except the last 10 base pairs. Sequence homology is 90%. Five mismatches result from a short duplication of the sequence AGCTC in TURF 2H3 at position 2309. Somewhat less homology is observed with *S. oligorhiza* and *E. gracilis*. The significant homology with chloroplast tRNAs from various species suggests that this portion of TURF 2H3 originated from the maize chloroplast genome. Direct comparison with maize chloroplast tRNA-Arg sequence has not been possible.

It can be seen that significant portions of the TURF 2H3 sequence are in fact composed of fragments of the coding and flanking regions of a number of functionally unrelated genes. While these derived segments cannot themselves be considered unique, their combination within a single sequence, TURF 2H3, is unique and further appears to have functional consequences inasmuch as transcripts arising from TURF 2H3 are known to be unique to cms-T stocks of maize. Because of the uniqueness of the TURF 2H3 sequence, it is possible to use the sequence, either in its entirety or subclones thereof, as probes to identify whether an unknown maize stock carries a male sterile cytoplasm of the T type. The identification can be made by means of Southern hybridization analysis using TURF 2H3 or a subclone thereof as a probe for hybridization with mitochondrial DNA of the unknown maize source (stock). Alternatively, RNA of the known stock (either total RNA or mtRNA) can be tested, by means of Northern hybridization Using 913T-41 as a probe for hybridization, or any subclone comprising the 913T-41 sequence or portion, preferably at least 14 bases, thereof.

A subclone is any consecutive sequence of nucleotides found within TURF 2H3 of at least 10–15 bp, and preferably at least 14 bp, length capable of serving as a probe for its homolog. A subclone may be a restriction fragment of TURF 2H3, a random DNAse-generated fragment, a synthetic sequence or a fragment generated by other means, known in the art. Conditions used for hybridization depends upon the length of the probe and it sequence, but will be readily determined for any given probe by those of ordinary skill in the art, see e.g., *Nucleic Acid Hybridization*, (B. P. Hames and S. J. Higgins eds.) IRL Press, Washington, D.C. (1985).

There are numerous ways in which TURF 2H3 or subfragments thereof can be used to probe mitochondrial DNA of an unknown variety to determine whether that variety carries the cms-T trait. Although several alternatives are illustrated herein, it will be understood by those of ordinary skill in the art that other strategies may be employed, following the teachings and disclosures herein. Specifically, subclones of TURF 2H3 other than those specifically described herein may be used for Southern blot analysis, and other forms of analysis, including DNA-RNA hybridization may be employed as a test system for distinguishing varieties carrying T-type cytoplasm from other forms of male sterility or from normals.

Figure 2:
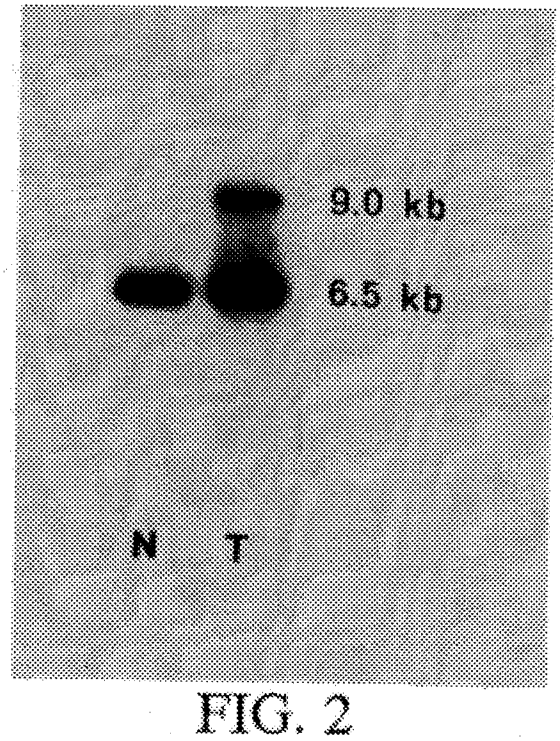
FIG. 2 shows hybridization of clone 913T-17 (FIG. 1) to BamHI restriction digests of normal (N) and cms-T maize mtDNA. Clone 913T-17 is interior to the repeat common to TURF 2H3 and the 5' flank of atp 6.

Three subclones of TURF 2H3 were chosen to demonstrate operational features of the invention: 913T-41, 45Sma-6 and 913T-17, whose size and location are shown diagrammatically in FIG. 1. FIG. 2 shows the results of a Southern blot hybridization in which BamHI restriction digests of normal and cms-T maize mtDNA were hybridized to labeled DNA of clone 913T-17. In the lane marked N, the mtDNA of a normal maize strain yielded but one BamHI fragment, of 6.5 kb, to which the probe hybridized. By contrast, cms-T mtDNA yielded two BamHI fragments, of 6.5 kb and 9.0 kb. The 6.5 kb band found in both normal and cms-T mtDNA corresponds to BamHI fragment known to carry the atp6 gene, since the probe in this experiment spans a region of TURF 2H3 carrying a sequence homologous to the 5' flank of atp6. The 9.0 kb band is in fact the 9.0 kb TURF 2B fragment which is known to contain TURF 2H3. It will be understood that TURF 2H3 and any clone thereof will hybridize with a 9.0 kb BamHI fragment from cms-T mtDNA, since that fragment contains TURF 2H3 and will not hybridize to such a fragment in normal, cms-S or cms-C mtDNA since TURF 2H3 is found only in cms-T mtDNA.

Figure 3:
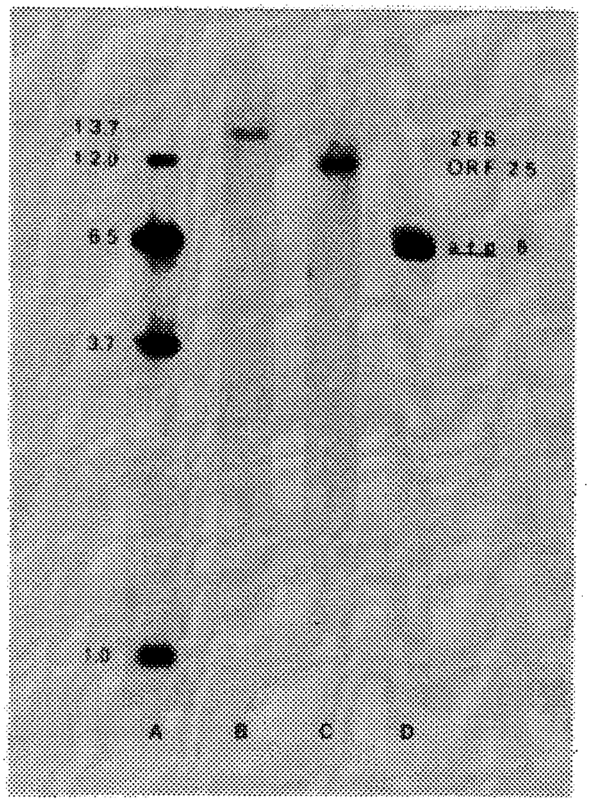
FIG. 3: Panel A represents hybridization of clone TURF 2B to a BamHI mtDNA blot of normal maize cytoplasm. Approximate sizes are indicated in kb. Panels B–D show hybridization of clones 913T-41, 45Sma-6 and 913T-17 (FIG. 1) respectively, to BamHI mtDNA digests of normal maize.

FIG. 3 shows the results of Southern hybridizations of TURF 2B (lane A), clone 913T-41 (lane B), clone 45Sma6 (lane C) and clone 913T-17 (lane D) to BamHI digested mtDNA of normal maize cytoplasm. In lane A, it is seen that TURF 2B does not exist in normal maize cytoplasm since no BamHI fragment of 9 kb with homology to TURF 2B was obtained from normal cytoplasm. On the other hand, sequences with homology to TURF 2B were observed in BamHI fragments of 1.0, 3.7, 6.5, 12.0 and 13.7 kb, respectively. Clone 913T-41 (lane B), a subclone of TURF 2H3 containing sequences homologous to the 26S ribosomal RNA gene hybridizes uniquely with a 13.7 kb BamHI fragment of normal cytoplasms. Again, no hybridization with a 9.0 kb BamHI fragment was observed, although such hybridization will occur with BamHI fragments of cms-T mtDNA. Clone 45Sma6 (lane C), which contains the sequences of ORF25 within TURF 2H3 hybridizes to a 12.0 kb BamHI fragment of normal mtDNA. Clone 913T-17 (lane D), containing the 5' flanking repeat common with atp6 hybridizes to the 6.5 kb atp6-containing BamHI fragment of normal cytoplasm. None of the subclones of TURF 2H3 were seen to hybridize with a 9.0 kb BamHI fragment; however, such hybridization will occur to BamHI fragments of mtDNA from cms-T varieties.

Figure 4:
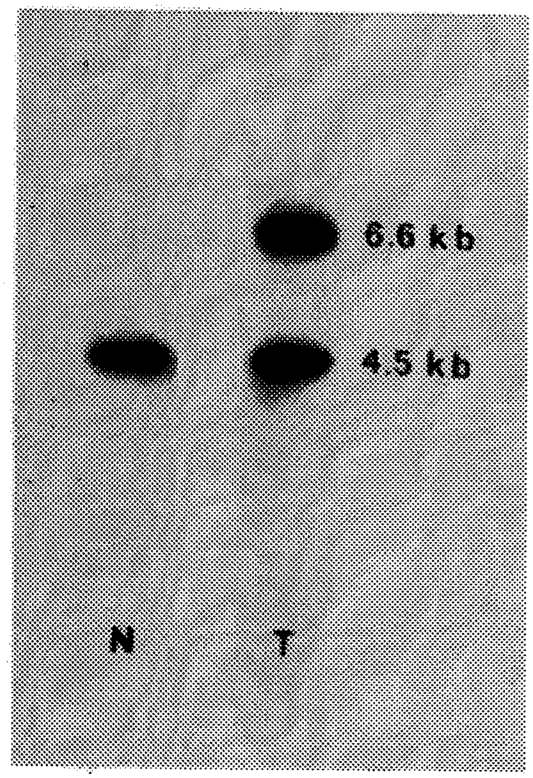
FIG. 4 shows hybridization of the 2013 bp HindIII fragment of TURF 2H3 (FIG. 1) to XhoI restriction digests of normal (N) and cms-T (T) maize mtDNA.

A hybridization test to definitively identify cms-T varieties can also be run using XhoI restriction digests. In FIG. 4, a 2013 bp HindIII fragment of TURF 2H3, extending from the left end to the first HindIII within ORF25 (see FIG. 1) was used to probe XhoI restriction digests of normal (N) and cms-T (T) maize mtDNA. Major fragments of 6.6 kb and 4.5 kb were detected in cms-T, while only a single major band of 4.5 kb was seen in normal. Minor bands were also observed in both lanes due to cross-hybridization of the fragments encoding the 26S ribosomal gene and ORF25. The entire 3.5 kb region of TURF 2H3 hybridizes to the 6.6 kb fragment in cms-T, while only subclones containing the repeated segment homologous to the 5' flank of atp6 hybridize to the 4.5 kb fragment in normal and T cytoplasm (data not shown). Therefore, the experiments disclosed herein demonstrate that the 6.6 kb XhoI fragment of cms-T mtDNA contains the unique TURF 2H3 sequence of T cytoplasm. This discovery forms the basis for an assay based upon Southern hybridization of TURF 2H3 or subclones thereof to XhoI digests of mtDNA from maize varieties to be tested.

In general any restriction digest of mtDNA can be probed with TURF 2H3 or a subclone thereof to test for the presence cms-T. It will be understood that some restriction enzymes, especially those with many sites within TURF 2H3 will yield small fragments which cannot be resolved by gel electrophoresis from fragments generated from normal, cms-C or cms-S mtDNA. Use of these enzymes can be avoided by those of ordinary skill in the art by referring to the sequence of Table 1, or by the use of simple tests.

Another, preferred, method to identify the presence of cms-T in a maize stock is by the method of Northern hybridization. The method exploits the fact that a region within TURF 2H3 is uniquely transcribed in cms-T cells. The uniquely transcribed region includes ORF 13 and is largely included within the cloned segment designated 913T-41 (See FIG. 1). The test employs known techniques of mRNA extraction, probe DNA labeling and Northern hybridization, using as probe DNA either clone 913T-41 or an equivalent thereof, comprising sufficient uniquely transcribed DNA to retain specificity of hybridization. It is well known in the art that conditions of hybridization can be adjusted to obtain a desired specificity, depending on the length of the homologous sequence, the percent of homology and the base composition of the sequence. In principle, as short a sequence as 10–15 nucleotides can be used, preferably at least 14, and such a sequence may be obtained as a subclone of TURF 2H3 or of 913T-41 or chemically synthesized. Longer sequences are preferred, and sequences having at least 80% homology to 913T-41 are acceptable substitutes. However, it will be understood that probes carrying sequences within TURF 2H3 but outside of 913T-41 may yield false positive results when used to probe mRNA because, as disclosed herein, some of the sequences within TURF 2H3 are homologous to commonly transcribed genes. Either total cellular RNA or mitochondrial mRNA can be used. The probe may be either the cloned mtDNA sequence itself, isolated from the vector that normally is used to carry it, or the vector or part thereof comprising the cloned mtDNA may be used as the probe, provided there are no other sequences within the vector homologous to mitochondrial mRNA. The probe DNA may be labeled by end-labeling, nick-translation or by any other means known to the art suitable for DNA-RNA hybridization.

Northern blot analysis revealed that clone 913T-41 hybridized uniquely to mitochondrial mRNA of cms-T maize, both restored and non-restored, but did not hybridize to mRNA of normal, cms-C, or cms-Vg (S-type) mitochondria. A 17-nucleotide synthetic oligomer, complementary to positions 1400 to 1416 of TURF 2H3 and located in the middle of ORF 13, gave the same hybridization pattern as clone 913T-41. Several bands were observed, notably bands corresponding to 1.1, 1.5, 1.8, 2.0 and 3.9 kb. When restored lines were tested., both 913T-41, the 17-mer (5'-CGTGGCCCTGCATGAGC-3') and a synthetic 21-mer complementary to positions 1235 to 1255, located near the 5' end of ORF 13 hybridized to mtRNA blots. The sequence from 1235 to 1255 is 5'-CCTTCTCCCTTTGATCAAGG-3'. The sizes of some transcripts differed between sterile and restored lines, indicating that perhaps the effect of restorer genes is on the nature of the transcripts, but the results demonstrated that both sterile and restored cms-T lines can be detected by the disclosed method of Northern hybridization. By contrast, the clone, 913S-50 (which includes a part of the 5'-end of ORF 25), and 45Sma-6 (in the 3'-end of ORF 25) (see FIG. 1) each hybridized to mRNA of other cms lines and normal maize. The fertility-restored line used in these experiments was B-37 cms-T (Rf1 Rf1 Rf2 Rf2).

Preparation of mitochondria:

Mitochondrial DNA was prepared from 6–7 day old dark grown seedlings of *Zea mays* L. using standard techniques as described, e.g., by Wilson, A. J. et al., (1984) Plant Cell Rep. 3:237–239; Lonsdale, D. M. et al. (1986) Methods Enzymol. 118:453–470.

Extra-mitochondrial DNA was digested by addition of MgCl2 to 10 mM, and deoxyribonuclease I (Worthington, DPFF) to 50 μg/ml. After 15–60 minutes incubation at room temperature, $Na_2EDTA$ was added to 10 mM, and mitochondria were pelleted by centrifugation. The mitochondria were then twice pelleted, with resuspension in buffer C, (sucrose, 0.20M; Tris-HCl, 0.05M, pH 7.5) to inactivate the deoxyribonuclease.

Preparation of mtDNA:

Mitochondria were resuspended in lysis buffer (0.05M Tris-HCl, 0.02M $Na_2EDTA$, pH 8.0) and Proteinase K (EM Laboratories, Inc., Elmsford, New York) was added to 200 μg/ml. Digestion proceeded for 30 minutes at room temperature, the preparation was frozen or immediately prepared for preparative CsCl-ethidium bromide centrifugation. Cesium chloride was added to lysed mitochondria preparations to an approximate density of 1.610 g/cm$^3$, and stored at 0° for 2–3 hours. In dim light, ethidium bromide was added to 200 μg/ml, and solid CsCl or buffer was added to adjust the density to 1.610 g/cm$^3$, as determined refractometrically. The preparation was transferred to cellulose nitrate or polyallomer tubes, covered with mineral oil, and centrifuged for 40 hours at 44,000 rpm at 20° C. in a Beckman 65 or ti75 rotor in a Beckman L2-65B or L5-50 ultracentrifuge. The fluorescing DNA bands, as detected with long-wave UV light, were then recovered. Ethidium bromide was removed by three successive extractions with isopropanol, followed by dialysis against restriction buffer to remove the CsCl. The preparations were then deproteinized by three successive chloroform-isoamyl alcohol (24:1 v/v) extractions, after bringing the solution to 1.0M sodium perchlorate. The preparations were dialyzed against restriction buffers for 48 hours, with buffer changes twice per day, or were pelleted at 50,000 rpm in the ti75 rotor for 18 hours at 4° C. All maize lines employed in this study are widely available from non-profit sources such as Illinois Foundation Seed, P.O. Box 722, Champaigne, Ill. 61820; Holdens Foundation Seed, P.O. Box 839, Williamsburg, Iowa; and Ohio Foundation Seed, P.O. Box 6, Croton, Ohio 43013.

The following sterile (non-restored) maize lines or crosses were used as sources of male-sterile cytoplasm: B73 x Mo17 (cms-C), B73 (cms-Vg), B73 (cms-T), and B37 (cms-T). The cms-Vg cytoplasm is a member of the S group of male sterile cytoplasms. B37 (cms-T) Rf1 Rf1 Rf2 Rf2 and B73 X Ky21 (cms-T) Rf1 Rf2 were used as sources of the cms-T restored cytoplasm; they are male fertile. The fertile hybrid, B73 X Mo17 (normal), was used as a source of male-fertile cytoplasm.

Preparation and Screening of mtDNA Library:

A DNA library was constructed from BamHI digests of total maize mtDNA cloned into the plasmid vector pUC9 (Vieira, J. and Messing, J. (1982) Gene 19:259). Ligated DNA was used to transform *E. coli* strain JM83, Ampicillin-resistant, Lac-colonies were selected, replicated, and fixed onto nitrocellulose filters (see, Maniatis, T. et al. (1982) in *Molecular Cloning: A Laboratory Manual*, Cold Spring Harbor Laboratory, Cold Spring Harbor, N.Y.). Colonies were screened by hybridization with total mtRNA, 5'-end labeled with [$\gamma$-$^{32}$P]ATP, 7000 Ci/mmol, using T4 polynucleotide kinase and hybridized to the fixed colonies at 50° C. in a hybridization solution containing 0.75M NaCl, 75 mM sodium citrate, 0.02% (w/v) bovine serum albumin, 0.02% (w/v) Ficoll, 0.02% (w/v) polyvinylpyrrolidone (pH 6.5) and 50% (v/v) formamide.

Gel electrophoresis and nucleic acid hybridizations

DNA fragments were separated by electrophoresis on 0.8% (w/v) agarose gels in TPE buffer (80 mM Tris-phosphate, 8 mM EDTA, pH 7.8) and transferred to nitrocellulose according to Wahl et al. (1979) Proc. Natl. Acad. Sci. USA 76:3683. MtRNA was heat denatured and fractionated by electrophoresis in 1.2% (w/v) agarose gels containing 6% (v/v) formaldehyde and blotted to nitrocellulose as described by Thomas (1980) Proc. Natl. Acad. Sci. USA 77:5201. Double-stranded DNA was labeled with [$\alpha$-$^{32}$P]-dATP (3200 Ci/mmole) by nick translation (Rigby et al. (1977) J. Mol. Biol. 113:237). Single-stranded DNA clones in the bacteriophage M13 were labeled by the backpriming technique of Hu and Messing (1982) Gene 17:281.

Nucleic acid hybridizations were performed under conditions already described (Dewey et al. (1985) Proc. Natl. Acad. Sci. USA 82:1015). The 18S (1986 nucleotides) and 26S (3546 nucleotides) ribosomal RNAs of maize mitochondria were used as markers for estimating RNA sizes. HindIII digests of bacteriophage lambda DNA were used as markers for estimating DNA sizes.

Oligonucleotide synthesis and hybridization

Oligonucleotide probes were prepared with the Applied Biosystems 380A DNA Synthesizer according to the manufacturer's instructions. Oligonucleotides were 5' end-labeled with [$\gamma$-$^{32}$P]ATP (7000 Ci/mmol) using T4 polynucleotide kinase (Maxam and Gilbert (1980) Meth. Enzymol. 65:499). Northern blots were prehybridized in a solution containing 6× NET (0.75 NaCl, 75 mM Tris-HCl pH 7.8, 1 mM EDTA), 5× Denhardts (0.1% bovine serum albumin, 0.1% Ficoll, 0.1% polyvinylpyrrolidone), 0.1% (w/v) sodium dodecyl sulfate (SDS) and 100 mg/ml salmon sperm DNA for 5 hours at 68° C. Labeled oligonucleotides were hybridized at 53° C. in a solution containing 6× NET, 5× Denhardts and 0.1% (w/v) SDS. Filters were washed in 6× SSC, 0.1% (w/v) SDS at room temperature.

DNA sequence analysis

Cloning for sequence analysis was carried out using M13 bacteriophage vectors mp10 and mp11 (Messing (1982) in *Genetic Engineering, Principles and Methods*, (J. K. Setlow and A. Hollaender, eds.) Plenum, New York, pp. 19). Ligation and transformation procedures were as outlined by New England Biolabs, Beverly, Mass. DNA sequences were determined by the chain-termination method of Sanger et al. (1977) with a universal primer (PL Biochemicals, Milwaukee, Wis.). Sequencing gels were either 6% (w/v) or 8% (w/v) polyacrylamide and 0.4 mm thick.

Nucleotide and amino acid sequence analyses were performed by computer programs furnished by Bionet (Intelligenetics Inc., 1975 El Camino Real West, Mountain View, Calif. 94040-2216). Bionet accesses the NIH (GenBank) and European Molecular Biology Laboratories (EMBL) DNA sequence libraries and the National Biomedical Research Foundation (NBRF) protein sequence database.

Polymerase chain reaction (PCR) technology provides powerful tools for the amplification and/or detection of nucleic acid sequences. PCR is well known to the art, and has been described (e.g., in Sambrook et al. (1989) *Molecular Cloning: A Laboratory Manual*, Cold Spring Harbor, N.Y., Cold Spring Harbor Laboratory Press, Chapter 14; U.S. Pat. Nos. 4,683,202 and 4,683,195, all of which are incorporated by reference herein. The major product of amplification is a double-stranded DNA molecule whose ends are determined by the 5' ends of the oligonucleotide primers and whose length is determined by the distance between the two primers. It is understood that to most effectively amplify a particular DNA sequence, the primers are unique to the particular DNA sequence or to the regions flanking that target DNA.

Under standard conditions using tag DNA polymerase, the polymerase becomes limiting after 25–30 cycles (or about $10^6$-fold amplification). To achieve further amplification, a sample of the amplified reaction mixture can be diluted $10^2$ to $10^3$ -fold for use as template in a fresh PCR. One can thus achieve $10^9$–$10^{10}$-fold amplification, and one can ultimately detect an initial single copy of the target sequence in the presence of $10^{13}$-fold excess of background DNA using Southern hybridization.

PCR can also be used to amplify segments of cloned DNA. Careful choice of primer sequences effectively results in the elimination of sequences flanking the target sequence. Predetermined deletion mutations can be generated as can fragments suitable for further cloning, e.g., with specifically engineered restriction sites in the flanking regions.

It is possible to amplify target sequences where the primer sequence is not a perfect match to the sequences flanking the target DNA by manipulation of annealing temperature and ramping time (the time to raise from annealing temperature to Taq polymerase reaction temperature. Optimization of reaction parameters is understood in the art.

Oligonucleotides for priming PCR can be as short as about 16 nucleotides, and are preferably 20–24 nucleotides long. Generally the annealing step is carried out at from 37°–55° C., and the Taq polymerase reaction is carried out at about 72° C. The oligonucleotide primer must be long enough to remain annealed to the template at the polymerase reaction temperature.

Target DNA can be added to the PCR as single-stranded or double-stranded molecules. Size is not crucial, but in general, high molecular weight DNA performs best if cut at least with a restriction enzyme which cuts rarely. In addition, linear DNA is more effective than circular DNA as a template.

Where amounts of sample tissue are too small to permit DNA or RNA extraction for Southern blots, DNA can be extracted and amplified by PCR to permit subsequent Southern hybridization for the detection of T-type cytoplasm. For such applications, the primers should be chosen to flank a target DNA sequence which is of a size unique to, and/or characteristic of T-type cytoplasm. For example, the ORF13 coding region could be amplified by PCR using a 24 base oligonucleotide immediately 5' to the ATG and a 24 base oligonucleotide whose sequence is taken from the region just 3' to the termination codon, but using the sequence of the noncoding strand rather than the coding strand.

PCR Amplification of ORF 13

DNA can be prepared from cms-T maize mitochondria or from cms-T maize tissue by any means known to the art, and what is added to the PCR should not contain significant amounts of chelating agents or multivalent anions. 10 mM Tris-Cl (pH7.6), 1 mM EDTA (pH8) is appropriate for dissolving sample DNA. Target DNA is cut with DraI, NotI or another restriction enzyme which cuts rarely, and which does not cut in the target region. Typically, control reactions are used to check sensitivity (1 μg, 0.1 μg, 0.01 μg, etc.).

Oligonucleotides to be used as PCR primers are synthesized (e.g., by automated DNA synthesis or by manual solid phase synthesis, as known to the art) which the following sequences:

5'-CATGAAATGGGTGAAGTCTCTTTC-3', taken from about 68 to about 44 bases upstream of the ORF13 ATG, and 5'-AAGAGAAAGGGAGACTTTGGTCCC-3' taken just 3' to the termination codon of ORF13.

Each primer is used as a concentration of 1 μM (micromlar) in the reaction. The standard PCR buffer is 50 mM KCl, 1 mM $MgCl_2$, 10 mM Tris-Cl (pH 8.3, room temperature). Either native Taq polymerase or a genetically engineered derivative (e.g., AmpliTaq™), can be used. dNTPs are added at final concentrations which are saturating for the reaction (200 μM each). Stock dNTP solutions should be neutralized with 1N NaOH so that the PCR reaction pH (at 72° C.) does not drop below pH 7.1.

100 μl reactions are prepared in sterile 0.5 ml microfuge tubes including appropriate volumes of sterile water, 30 μl; 10× buffer, 10 μl; $dNTP_5$, 1.25 mM each, 16 μl; primer 1, 100 pmoles in 5 μl $H_2O$; primer 2, 100 pmoles in 5 μl $H_2O$; template DNA, up to 2 μg; sterile water up to 100 μl.

The mixture is heated 5 min at 94° C. to denature DNA completely. While at 94° C., 0.5 μl Taq polymerase (5 units/μl) is added. Then the mixture is overlayered with 100 μl light mineral oil (e.g., M-3516, Sigma Chemical Co., St. Louis, Mo.) to prevent evaporative loss. Primers are allowed to anneal at 50° C. for 2 min; the temperature is then raised to 72° C. and the polymerization reaction is allowed to proceed for 3 min.

Subsequent cycles include 1 min denaturation at 94° C., 2 min annealing at 50° C., 3 min polymerization at 72° C. The final cycle allows 1 min denaturation and 2 min annealing, but 10 min polymerization. Times are measured after temperature equilibration. If necessary, the oil can be removed by extraction with 150 μl chloroform. The aqueous phase forms a micelle near the meniscus, which can be removed.

Generally, 25 cycles for amplification of single copy target sequences in eukaryotic or genomic DNA allow detection on agarose or polyacrylamide gels. Southern hybridization or sequencing can also be used for product analysis.

The use of the disclosed primers will yield an amplified product of about 440 bp, detectable by agarose gel electrophoresis, and/or by Southern hybridization using techniques known to the art.

If samples do not contain T-type mitochondrial DNA, no such approximately 440 bp DNA product will be made.

It will be understood that the genetic function and the test utility of the sequences described and claimed homologous sequences are obtainable by means known in the art. Both laboratory-made and naturally-occurring homologs having the functional properties, and the utility disclosed herein will be recognized as equivalents to compositions claimed herein.

TABLE 1

Nucleotide Sequence of the Maize TURF 2H3 Fragment

| | | | | | | | | | | |
|---|---|---|---|---|---|---|---|---|---|---|
| TYAF 2N3 | 1 | 5'-AAGCTTTAGG | TAGTTCGCCG | TGCGATGGGC | CTGAGGATCT | ATTCCAAAGG | GTGATGGGTC | GTGGGTACGA | | |
| | – | ********** | ********** | ********** | ********** | ********** | ********** | ********** | | |
| atp 6 | −1589 | 5'-AAGCTTTAGG | TAGTTCGCCG | TGCGATGGGC | CTGAGGATCT | ATTCCAAAGG | GTGATGGGTC | GTGGGTACGA | | |
| | 71 | CTCTTCAGAA | GGCGCTTTTG | CCAACCACCG | AGCACCAACA | AATGAAGAGA | GTTACCACAA | GTATGAGACC | ACTGAAACTA | CTTCGCCTGC |
| | | ********** | ********** | ********** | ********** | ********** | ********** | ********** | ********** | ********** |
| | −1519 | CTCTTCAGAA | GGCGCTTTTG | CCAACCACCG | AGCACCAACA | AATGAAGAGA | GTTACCACAA | GTATGAGACC | ACTGAAACTA | CTTCGCCTGC |
| | 161 | TTTGAATCAG | AGCAAACTGC | TTTTCAGTAT | AAGACCACCA | ATCTAGTACG | CAACCATTGC | CTATTATGCC | ATCCATATTG | TTGACTTTCA |
| | | ********** | ********** | ********** | ********** | ********** | ********** | ********** | ********** | ********** |
| | −1429 | TTTGAATCAG | AGCAAACTGC | TTTTCAGTAT | AAGACCACCA | ATCTAGTACG | CAACCATTGC | CTATTATGCC | ATCCATATTG | TTGACTTTCA |
| | 251 | CAGACCCACT | ATGACTGCCT | ACGCCCATAT | AGATAGAGAA | AAGTTCACCT | AAGGATAATA | AAACGTTTGA | GGAAGGTTAC | CGCTTACGAT |
| | | ********** | ********** | ********** | ********** | ********** | ********** | ********** | ********** | ********** |
| | −1339 | CAGACCCACT | ATGACTGCCT | ACGCCCATAT | AGATAGAGAA | AAGTTCACCT | AAGGATAATA | AAACGTTTGA | GGAAGGTTAC | CGCTTACGAT |
| | 341 | ATACCTATAT | ATAGATAGTG | TAGTGTTGTA | GTGTGTTAAG | TAGATCGGTC | CCATATAAAG | TTGCAATGTA | TCTGCAATGA | GTTCATCTAC |
| | | ********** | ********** | ********** | ********** | ********** | ********** | ********** | ********** | ********** |
| | −1249 | ATACCTATAT | ATAGATAGTG | TAGTGTTGTA | GTGTGTTAAG | TAGATCGGTC | CCATATAAAG | TTGCAATGTA | TCTGCAATGA | GTTCATCTAC |
| | 431 | TCCGGGGTGT | TCTCCGCACT | TCTCAAGAAA | GAAATAGTTG | GAAATTCCCC | GGATCGTCTG | CGCTTGGCTT | GGTATTCTTA | TACTGAATCG |
| | | ********** | ********** | ********** | ********** | ********** | ********** | ********** | ********** | ********** |
| | −1159 | TCCGGGGTGT | TCTCCGCACT | TCTCAAGAAA | GAAATAGTTG | GAAATTCCCC | GGATCGTCTG | CGCTTGGCTT | GGTATTCTTA | TACTGAATCG |
| | 521 | CTGTTGGATA | AAAGAAAGCA | TAAAGTTTTT | AAGCCTGCGT | TCTCGTTGGC | GAAACCACTA | GGAGGCAACC | ATGAAAGCGG | TTTCTATGTT |
| | | ********** | ********** | ********** | ********** | ********** | ********** | ********** | ********** | ********** |
| | −1069 | CTGTTGGATA | AAAGAAAGCA | TAAAGTTTTT | AAGCCTGCGT | TCTCGTTGGC | GAAACCACTA | GGAGGCAACC | ATGAAAGCGG | TTTCTATGTT |
| | 611 | TCGATCGAAC | CAACACAGCT | TTACGCTTCT | TTCCAACTCT | ACCCACGCTT | CGGGTTCGCA | CTTACTTTAC | GCCTTACCGA | ACTTGGGCTT |
| | | ********** | ********** | ********** | ********** | ********** | ********** | ********** | ********** | ********** |
| | −979 | TCGATCGAAC | CAACACAGCT | TTACGCTTCT | TTCCAACTCT | ACCCACGCTT | CGGGTTCGCA | CTTACTTTAC | GCCTTACCGA | ACTTGGGCTT |
| | 701 | AGTTCAGCCA | GCTTCGTAAC | ATGCCTGCTC | AAAGTGAGTA | GTTGGAAGTT | CCTGTAAGCA | TCTTCCCATG | AATTGACGTA | TATAAGCGTA |
| | | ********** | ********** | ********** | ********** | ********** | ********** | ********** | ********** | ********** |
| | −889 | AGTTCAGCCA | GCTTCGTAAC | ATGCCTGCTC | AAAGTGAGTA | GTTGGAAGTT | CCTGTAAGCA | TCTTCCCATG | AATTGACGTA | TATAAGCGTA |
| | 791 | GTTATCAGGT | ACGCCGTGAG | CTGGATTCTA | TCCCCGAGGA | TAGAGATTGA | TGGGTAATAG | TTTTGATAGA | AAACTCGTAT | GTTAAGTTCT |
| | | ********** | ********** | ********** | ********** | ********** | ********** | ********** | ********** | ********** |
| | −799 | GTTATCAGGT | ACGCCGTGAG | CTGGATTCTA | TCCCCGAGGA | TAGAGATTGA | TGGGTAATAG | TTTTGATAGA | AAACTCGTAT | GTTAAGTTCT |
| | 881 | CTAGTTGATG | TGATGCGGCT | CGATTCATCA | TTGCTCTCAC | ATCAATGTTT | TCGGTTCCCT | TTTTACTCTC | CCATTTTCAT | AGAGAAAGAT |
| | | ********** | ********** | ********** | ********** | ********** | ********** | ********** | ********** | ********** |
| | −709 | CTAGTTGATG | TGATGCGGCT | CGATTCATCA | TTGCTCTCAC | ATCAATGTTT | TCGGTTCCCT | TTTTACTCTC | CCATTTTCAT | AGAGAAAGAT |
| | 971 | GTTCTGATTC | AGTTCTCTCT | GAAAAGGAAG | ACGGGGCCCT | TAGCTTAGGG | ACACAGTAGT | ACCATTTCCA | TTGTGCGAAA | GGTCGTGTCC |
| | | ********** | ********** | ********** | ********** | ********** | ********** | ********** | ********** | ********** |
| | −619 | GTTCTGATTC | AGTTCTCTCT | GAAAAGGAAG | ACGGGGCCCT | TAGCTTAGGG | ACACAGTAGT | ACCATTTCCA | TTGTGCGAAA | GGTCGTGTCC ↓ |

TABLE 1-continued

Nucleotide Sequence of the Maize TURF 2H3 Fragment

```
1061  TGGTAGCCTC TCTGCTGTAG ACGGTCTCAT TGGTAAATTC TTCCATTTCT GAAATTGTCA AATCGAGATT GTGTGGGTGT TCAGTTCATG
      ********** ********** ********** ********** ********** ********** ********** ********** *****
-529  TGGTAGCCTC TCTGCTGTAG ACGGTCTCAT TGGTAAATTC TTCCATTTCT GAAATTGTCA AATCGAGATT GTGTGGGTGT TCAGT

                ↓                                                             ORF 13 met ile thr thr phe leu asn
1151  AAATGGGTGA AGTCTCTTTC AAGAAAAGAG CAGAG-GGAG CGGAAAGGAA AACACTTTTT CGTCA ATG ATC ACT ACT TTC TTA AAC
                 ********** ** ******* * *** **     *******  ** ******* ***** *** *** *** *** *** *** ***
      265   4170 AGTCTCTTTC AACAAAAGAG CGGAGCGG-- ---AAAGGAA AAAACTTTTT CGTCA ATG ATC ACG ACT TTC TTA AAC

      leu pro pro phe asp gln gly leu val phe phe gly ser ile phe ile phe phe leu cys ile leu leu ile lys
1236  CTT CCT CCC TTT GAT CAA GGT TTG GTA TTT TTC GGT TCT ATT TTT ATT TTT TTT TTG TGC ATA TTA TTG ATA AAG
      *** *** *** *** ***  ** *** *** *** *** *** *** *** *** ***   *  **  **  ** * *  **          * **  **
4241  CTT CCT CCC TTT GAT AAA GGT TTG GTA TTT TTC GGT TCT ATT TTT GTG TTC ATT TTT TTC ATT AGG CAG ATT AAA

      gly tyr leu arg lys met asp asp ser tyr leu ala gln leu ser glu leu ala asn his asn arg val glu ala
1311  GGA TAT CTC CGT AAA ATG GAT GAT TCC TAT TTG GCT CAA CTC TCC GAG TTA GCC AAC CAC AAT AGA GTG GAA GCG
      *** *** **   ** **  **  **  **    * *** ***  ** *** **  **  *** **  *** *** *** *** *** *** *** ***
4316  GGA TAT CTA AGT AAG ATA GAC GAG AGC TAT TTG ACT CAA CTA TCT GAG TTT GCC AAC CAC AAT AGA GTG GAA GCG

      ala lys ala gly his val ala leu his glu leu ser phe ser              trp leu arg gly val gln ile arg val
1386  GCA AAA GCG GGC CAC GTG GCC CTG CAT GAG CTA TCC TTC TCG -----        TGG TTG AGG GGG GTT CAA ATT AGG GTG
      *** *** *** *** *** *** *** *** *** *** *** *** ***  **              *** *** *** *** ***  **  **  *** ***
4391  GCA AAA GCG GGC CAC GTG GCC CTG CAT GAG CTA TCC TTC TCA TCTCA        TGG TTG AGG GGG GTT AAA ATG AGG GTG

                                  ↓                                        ↓
      arg thr leu pro ile gln trp asn glu gly gly gly arg ser asn asp gln ser thr leu ser lys pro lys tyr
1455  AGG ACC TTA CCT ATA CAA CGG AAT GAA GGA GGG GGT CGA AGC AAC GAC CAA TCC ACT CTC TCT AAG CCT AAG TAT
      * * *** **  *** *** *** *** **                                       **  **  *** *   *** *** *** ***
4465  AAG ACC TTC CCT ATA CAA CGG AA                             265 1055  CC ACC CTC T-- AAG CCT AAG TAT

                                                  ↓
      ser ser met thr asp ser val gln val pro
1530  TCC TCA ATG ACC GAT AGC GTA CAA GTA CCG TGA GGGACCAAAG TCTCCCTTTC TCTTTTGGGG TGGGGGCGGA GCTGAATAAA
      *** *** *** *** *** *** *** *** *** *** *** **
1076  TCC TCA ATG ACC GAT AGC GTA CAA GTA CCG TGA GG

                            OMF 25  met arg phe ser gly met asp met lys lys arg lys met leu phe ala ala
1613  TTGTATTTTA TAAAGTTTAG AGTCACA ATG AGA TTT AGT GGA ATG GAT ATG AAG AAA AGA AAA ATG CTA TTT GCT GCT

      ile pro ser ile cys ala ser ser pro lys lys ile ser ile tyr asn glu glu met ile val ala arg cys phe
1691  ATT CCA TCT ATT TGT GCA TCA AGT CCG AAG AAG ATC TCA ATC TAT AAT GAA GAA ATG ATA GTA GCT CGT TGT TTT

      ile gly phe leu ile leu ser trp lys ser leu gly lys thr phe lys glu thr leu asp gly arg ile glu ser
1766  ATA GGC TTT CTC ATA TTA AGT CGG AAG AGT TTA GGT AAG ACT TTC AAA GAA ACT CTC GAC GGG AGA ATC GAG TCT

      ile gln glu ser leu gln gln phe cys asn glu val glu val ile leu glu glu ser asn glu gln gln arg leu
1841  ATT CAG GAA TCA TTG CAG CAA TTC TGC AAT CCT AAC GAA GTC ATT CTG GAG GAA TCC AAT GAA CAA CAA CGA TTA

      leu asn leu gln ile ser leu arg ile cys ser thr val lys val val glu ser leu pro ala ala arg cys ala
1916  CTT AAT CTA CAG ATC AGC TTG CGA ATT TGC AGC ACC GTA AAA GTA GTA GAA TCA TTA CCA GCG GCA CGC TGC GCG
```

TABLE 1-continued

Nucleotide Sequence of the Maize TURF 2H3 Fragment

```
      pro lys cys glu lys thr val gln ala leu leu cys arg asn leu asn val lys ser ala thr leu leu asn ala
1991  CCT AAG TGC GAA AAG ACA GTG CAA GCT TTG TTA TGC CGA AAC CTA AAT GTC AAG TCA GCA ACA CTT CTA AAT GCC

      thr ser ser arg arg ile arg leu gln asp asp ile val thr gly phe his phe ser val ser glu arg phe val
2066  ACT TCT TCC CGT CGC ATC CGT CTT CAG GAC GAT ATA GTC ACA GGT TTT CAC TTT TCA GTG AGT GAA AGA TTT GTA

      ser gly ser thr thr leu val glu ala ser thr val glu gln ile arg glu ala phe leu leu glu pro arg asp
2141  TCC GGG TCT ACT ACT TTG GTA GAA GCT TCT ACC GTA GAA CAA ATT CGA GAG GCC TTC TTA TTA GAA CCC AGA GAC

                                                              ↓
      leu ile arg glu gly phe ile val leu arg lys val arg val gly gly ile pro gly lys arg ser cys gly asp
2216  CTA ATT CGA GAA GGC TTT ATA GTC CTA AGA AAG GTG AGG GTG GGG GGT ATC CCC GGG AAG AGA TCC TGT GGA GAC
                                                               *  ***  *   **  ***  **  *** ***  ** *** ***
                           S. eligorhiza chloroplast tMMA- Arg   207    G  GGT ACT CCT GGG AAC AGA TCC GGT GGA GAC

      gly val     gly leu                                                                      ↓
2291  GGG GTG  -  GGC CTG TAG CTC AGCTC AGAGGATTAG AGCACGTGGC TACGAACCAC GGTGTTGGGG GTTCGAATCC AC TTCTGAGAAG
      *** ***     *** *** *** ***       ********** ********** ********** ***** **** **********
238   GGG GTG  G  GGC CTG TAG CTC ----- AGAGGATTAG AGCACGTGGC TACGAACCAC GGTGTCGGGG GTTCGAATCC

2376  GAAGTATTGG CTATGCACCC CTTCCCTTGA CTAACTAAGT CTGCATATAA GGAGTGCAGA AATTCAATAC TGTTCGTATC GCCGTGCAAA

2466  TTATACGCAA TTTGTTTCAT TGTAAACCCT TGGCCCTTCC AATTCACGCC CGGAGGAGTA TTACAATAGA CGTTGAAACA ACCCTGGAGC

2556  TTATCTGTAA TTTGCTCCTT GAGCGTTTCT AACGTCAATA AAATAAAGTC CTCCAACTTA TGATGCCAGT TTTCCGAAGC CGCGGCTTTT

2646  ACCCGCTTTA TAAGCGATGA GTAGGGCGAT GCATAAAAAG TCATATTTCT TGGTGTAGGG ATCTCATAGG AAAAGAGATA CCGAGGCCCA

2736  CCAACCGTAT ACTTGATTTA TGGTTTGGTG GGGAAAGAAG AGTGGGTATG GGGCTTCTTT CATGGTGCCA TTCTTTACTT TACGTAATAA

2826  AAATCAGAGA GGGACTGAAC ACTTGTTTTG ATCTACGAAG AGTTGAAAAA CAATTGAATT GCCTTTATTT GATCTTAAAG AATCGGCATT

2916  GGCTTCAGTT CAGATCTTAT GGGAAAAGGC GCGTAGCGAA GAAGTGTATG CTCAATAAAC TGAAGAAGCA TATATAAGAA AGAAGCCATC

3006  ATCACTATGT TTACTCCTAC CCAAGGAAGG AGGTCAGTCA AAGCAATGAA ATGAAGAGGC CGTGACCTAA TACCTATCTG TGTTCTCTTG

3096  GATAGTGGTC CAGTTTGAAT AGTTGTATAG TTATTTGTAA ACCCGGGGGC CCTGAAATTA GCCAAAACAA CCCGGTGGGG TAAAGTCGTC

3186  AAGTGGACTA TGGTTCACAA TAATAGTGAC TGACACGAGA TGCGATGCCA AGTTAGAAGG TCAAAAGTGA GAAAGTTGGA GGGGAGATGC

3276  CATGATCCTA GGTGTAGATT GGCTTATCAG CCTATGGCCA TTCCTTTAAT ACTTTTGAAC GATGACTTAA TGCTTCAAAG CCCTCCCCAT
```

TABLE 1-continued

Nucleotide Sequence of the Maize TURF 2H3 Fragment

| | | | | | | | | | |
|---|---|---|---|---|---|---|---|---|---|
| 3366 | ATAGCACAGC | CTTCGTAAGG | CTTATCACAC | TCGGGCCTGT | AACTGGAATC | TGAGCATTTC | TTGTTTGGGG | TTCGCAAACC | GACTTAAGTC |
| 3456 | TTTATTTTCT | AATAGGCTTG | GCCTTCGGGG | GAACAAAGCC | ATTCCATGGA | ACCTGAGACT | TTGATTCCAG | CCTACTTCTA | CTTGAAAAGC |
| 3546 | TT-3' | | | | | | | | |

We claim:

1. An isolated DNA molecule consisting of a nucleotide sequence which specifically hybridizes to a mtDNA restriction fragment of cms-T mtDNA, which restriction fragment is of a unique size in cms-T mtDNA, wherein said nucleotide sequence is selected from the group consisting of TURF 2H3, 913T-41, 913S-50, 45Sma-6, 913T-17 and ORF 13.

2. An isolated recombinant DNA molecule consisting of a nucleotide sequence of at least 14 contiguous nucleotides of TURF 2H3, wherein said nucleotide sequence specifically hybridizes to a mtDNA restriction fragment of cms-T mtDNA, which restriction fragment of cms-T mtDNA is of a unique size in cms-T mtDNA as compared with normal mtDNA and cms-T mtDNA.

3. An isolated DNA fragment consisting of at least 14 contiguous nucleotides of the nucleotide sequence of 913T-41, wherein said isolated DNA fragment specifically hybridizes to a mtDNA restriction fragment of cms-T mtDNA, which restriction fragment of cms-T mtDNA is of a unique size in cms-T mtDNA as compared with normal mtDNA and cms-t mtDNA.

4. The isolated DNA fragment of claim 3 consisting of a nucleotide sequence selected from the group consisting of SEQ ID NOS. 1–4.

5. The isolated DNA fragment of 3 consisting of the nucleotide sequence of ORF 13, from nucleotide 1215 to nucleotide 1560, as in Table 1.

6. An isolated DNA molecule useful as a probe comprising a nucleotide sequence which specifically hybridizes to a mtDNA restriction fragment of cms-T mtDNA, which restriction fragment is of a unique size in cms-T mtDNA, wherein said nucleotide sequence is selected from the group consisting of TURF 2H3, 913T-41, 913S-50, 45Sma-6, 913T-17 and ORF 13.

7. An isolated recombinant DNA molecule useful as a probe comprising a nucleotide sequence of at least 14 contiguous nucleotides of TURF 2H3, wherein said nucleotide sequence specifically hybridizes to a mtDNA restriction fragment of cms-T mtDNA, which restriction fragment of cms-T mtDNA is of a unique size in cms-T mtDNA as compared with normal mtDNA and cms-T mtDNA.

8. An isolated DNA molecule useful as a probe comprising at least 14 contiguous nucleotides of the nucleotide sequence of 913T-41, wherein said isolated DNA fragment specifically hybridizes to a mtDNA restriction fragment of cms-T mtDNA, which restriction fragment of cms-T mtDNA is of a unique size in cms-T mtDNA as compared with normal mtDNA and cms-t mtDNA.

9. The isolated DNA molecule of claim 8 comprising a nucleotide sequence selected from the group consisting of SEQ ID NOS. 1–4.

10. The isolated DNA molecule of claim 8 comprising the nucleotide sequence of ORF 13, from nucleotide 1215 to nucleotide 1560, as in Table 1.

11. A DNA vector comprising a nulceotide sequence which specifically hybridizes to a mtDNA restriction fragment of cms-T mtDNA, which restriction fragment is of a unique size in cms-T mtDNA, wherein said nucleotide sequence is selected from the group consisting of TURF 2H3, 913T-41, 913S-50, 45ma-6, 913T-17 and ORF 13.

12. A DNA vector comprising a nucleotide sequence of at least 14 contiguous nucleotides of TURF 2H3, wherein said nucleotide sequence specifically hybridizes to a mtDNA restriction fragment of cms-T mtDNA, which restriction fragment of cms-T mtDNA is of a unique size in cms-T mtDNA as compared with normal mtDNA and cms-T mtDNA.

13. A DNA vector comprising at least 14 contiguous nucleotides of the nucleotide sequence of 913T-41, wherein said isolated DNA fragment specifically hybridizes to a mtDNA restriction fragment of cms-T mtDNA, which restriction fragment of cms-T mtDNA is of a unique size in cms-T mtDNA as compared with normal mtDNA and cms-t mtDNA.

14. A DNA vector comprising a nucleotide sequence selected from the group consisting of SEQ ID NO. 1, SEQ ID NO. 2, SEQ ID NO. 3, and SEQ ID NO. 4.

15. A DNA vector comprising the nucleotide sequence of ORF 13, from nucleotide 1215 to nucleotide 1560, as in Table 1.

* * * * *

UNITED STATES PATENT AND TRADEMARK OFFICE

CERTIFICATE OF CORRECTION

PATENT NO. : 5,660,983

DATED : August 26, 1997

INVENTOR(S) : Charles S. Levings, III and Ralph Dewey

It is certified that error appears in the above-identified patent and that said Letters Patent is hereby corrected as shown below:

Column 8, line 6: "Using" should read --using--.

Column 10, line 16: "tested., both" should read --tested, both--.

Column 12, line 38: "tag" should read --Taq--

Column 25, Claim 5, line 4: "of 3 consisting" should read --of claim 3 consisting--

Column 26, Claim 11, line 9: "45ma-6" should read --45Sma-6--.

Signed and Sealed this

Twentieth Day of January, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 17 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:1:

CGTGGCCCTG CATGAGC 17

( 2 ) INFORMATION FOR SEQ ID NO:2:

( i ) SEQUENCE CHARACTERISTICS:
( A ) LENGTH: 21 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:2:

CCTTCCTCCC TTTGATCAAG G 21

( 2 ) INFORMATION FOR SEQ ID NO:3:

( i ) SEQUENCE CHARACTERISTICS:
( A ) LENGTH: 17 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:3:

GCACCGGGAC GTACTCG 17

( 2 ) INFORMATION FOR SEQ ID NO:4:

( i ) SEQUENCE CHARACTERISTICS:
( A ) LENGTH: 21 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:4:

GGAAGGAGGG AAACTAGTTC C 21